US012564634B2

(12) United States Patent
Lee

(10) Patent No.: US 12,564,634 B2
(45) Date of Patent: Mar. 3, 2026

(54) HIGHLY DISPERSIBLE ZINC PHTHALOCYANINE-SILICA NANOTUBES AND PREPARATION METHOD THEREFOR

(71) Applicant: Sang Ho Lee, Busan (KR)

(72) Inventor: Sang Ho Lee, Busan (KR)

(*) Notice: Subject to any disclaimer, the term of this patent is extended or adjusted under 35 U.S.C. 154(b) by 1089 days.

(21) Appl. No.: 17/617,540

(22) PCT Filed: Jun. 2, 2020

(86) PCT No.: PCT/KR2020/007124
§ 371 (c)(1),
(2) Date: Dec. 8, 2021

(87) PCT Pub. No.: WO2020/251202

PCT Pub. Date: Dec. 17, 2020

(65) Prior Publication Data

US 2022/0241419 A1 Aug. 4, 2022

(30) Foreign Application Priority Data

Jun. 12, 2019 (KR) ........................ 10-2019-0069045

(51) Int. Cl.
| | |
|---|---|
| A61K 41/00 | (2020.01) |
| A61K 47/52 | (2017.01) |
| A61K 47/69 | (2017.01) |
| B82Y 5/00 | (2011.01) |
| B82Y 30/00 | (2011.01) |
| B82Y 40/00 | (2011.01) |

(52) U.S. Cl.
CPC .......... *A61K 41/0071* (2013.01); *A61K 47/52* (2017.08); *A61K 47/69* (2017.08); *B82Y 5/00* (2013.01); *B82Y 30/00* (2013.01); *B82Y 40/00* (2013.01)

(58) Field of Classification Search
CPC .... A61K 41/0071; A61K 47/69; A61K 47/52; B82Y 5/00; B82Y 30/00; B82Y 40/00
See application file for complete search history.

(56) References Cited

FOREIGN PATENT DOCUMENTS

| | | | | | |
|---|---|---|---|---|---|
| KR | 10-2009-0051926 A | | 5/2009 | | |
| KR | 10-2010-0081644 A | | 7/2010 | | |
| KR | 2015010214 A | * | 1/2015 | ............ | B60K 17/08 |
| KR | 10-2015-0102514 A | | 9/2015 | | |
| KR | 20150102514 | * | 9/2015 | | |
| KR | 10-2094903 B1 | | 3/2020 | | |
| WO | 2015129998 A1 | | 9/2015 | | |

OTHER PUBLICATIONS

Ma X. et. al. Spacer Intercalated Disassembly and Photodynamic Activity of Zinc Phthalocyanine Inside Nanochannels of Mesoporous Silica ACS Appl. Mater. Interfaces 5:12860-12868 (Year: 2013).*
English translation of KR 2015010214 A provided by EPO (Year: 2025).*
X. Ma, et al. "Spacer Intercalated Disassembly and Photodynamic Activity of Zinc Phthalocyanine Inside Nanochannels of Mesoporous Silica," ACS Appl. Mater. Interfaces 5: 12860-12868 (Dec. 6, 2013). (Year: 2013).*
H. Choi, et al. "Novelty of Dynamic Process in the Synthesis of Biocompatible Silica Nanotubes by Biomimetic Glycyldodecylamide as a Soft Template," Langmuir 2017, 33, 10707-10714. (Year: 2017).*
Y. Xi, Z. Liangying, W. Sasa. "Pore size and pore-size distribution control of porous silica," Sensors and Actuators B 24-25 (1995) 347-352 (Year: 1995).*
Office Action issued for CN patent application Serial No. 202080043224.4, dated Dec. 13, 2022, with English Translation.
Van Hell, A.J., et al. "Peptide nanocarriers for intracellular delivery of photosensitizers" (2010, electronic publication Sep. 18, 2009) J. Controlled Release, vol. 141, pp. 347-353.
Ma, X., et al. "Spacer Intercalated Disassembly and Photodynamic Activity of Zinc Phthalocyanine Inside Nanochannels of Mesoporous Silica Nanoparticles" Applied Materials & Interfaces (2013) vol. 5, pp. 12860-12868.
International Search Report issued for PCT/KR2020/007124 dated Sep. 9, 2020.
Written Opinion of the International Searching Authority issued for PCT/KR2020/007124 dated Sep. 9, 2020.
Han, S.C., Park, S.E. "Synthesis and Characterization of Silica Nanotube by Glycyldodecylamide as a Template" Bull. Korean Chem. Soc. (2010) vol. 31, No. 12, pp. 3519-3520.

* cited by examiner

*Primary Examiner* — Michael P Cohen
(74) *Attorney, Agent, or Firm* — Westman, Champlin & Koehler, P.A.; Amanda M. Prose

(57) ABSTRACT

The present disclosure relates to highly dispersible zinc phthalocyanine-silica nanotubes and a preparation method thereof. More particularly, the present disclosure relates to highly dispersible zinc phthalocyanine-silica nanotubes capable of improving the dispersibility of zinc phthalocyanine so that the zinc phthalocyanine can be easily absorbed in the body, and to a method of preparing highly dispersible zinc phthalocyanine nanotubes. The present disclosure proposes a highly dispersible zinc phthalocyanine-silica nanotube and a method of preparing sample. The method includes a first step of mixing a template with a alcohol solution to prepare a nanotube solution containing a nanotube template, a second step of adding a zinc phthalocyanine (ZnPc) solution to the nanotube solution and stirring the resulting mixture to prepare a zinc phthalocyanine-silica nanotube solution, a third step of adding a silica precursor to the zinc phthalocyanine-nanotube solution and stirring the resulting mixture to induce silication, thereby preparing a zinc phthalocyanine-silica nanotube solution, and a fourth step of filtering and drying the zinc phthalocyanine-silica nanotube to prepare zinc phthalocyanine nanotube powder. Further proposed is a method of preparing the zinc phthalocyanine powder.

9 Claims, 10 Drawing Sheets

HIGHLY DISPERSIBLE ZINC PHTHALOCYANINE-SILICA NANOTUBES AND PREPARATION METHOD THEREFOR

CROSS-REFERENCE TO RELATED APPLICATION

This Application is a Section 371 National Stage Application of International Application No. PCT/KR2020/007124, filed Jun. 2, 2020 and published as WO/2020/251202 on Dec. 17, 2020, in Korean, which claims priority to KR Patent Application No. 10-2019-0069045 filed Jun. 12, 2019 the contents of which are hereby incorporated by reference in their entirety.

TECHNICAL FIELD

The present disclosure relates to highly dispersible zinc phthalocyanine-silica nanotubes and a preparation method thereof. More particularly, the present disclosure relates to highly dispersible zinc phthalocyanine-silica nanotubes capable of improving the dispersibility of zinc phthalocyanine so that the zinc phthalocyanine can be easily absorbed in the body, and to a method of preparing highly dispersible zinc phthalocyanine nanotubes.

BACKGROUND ART

Photosensitizers used in photodynamic therapy (PDT) include porphyrin derivatives, chlorins, porphycenes, and phthalocyanines (Pcs).

Among them, metallo phthalocyanine (MPc) is a ring substituent of phthalocyanine (Pc), and photodynamic properties thereof can be easily adjusted according to the type of a functional group and a central metal ion that can be introduced.

In particular, zinc phthalocyanine (ZnPc) has a closed d-shell structure and Zn(II) ion as a diamagnetic central metal ion. ZnPc is known to exhibit excellent photodynamic properties because the yield of the triplet electrical state having an extended lifetime essential for the generation of reactive oxygen species is excellent. Moreover, zinc phthalocyanine has a wide light absorption cross-sectional area in a tissue transmission spectrum range of 650 to 900 nm.

However, in photodynamic therapy, photosensitizers such as zinc phthalocyanine have a problem in that they are hydrophobic (that is, they do not dissolve well in water) and thus their solubility in blood and dispersibility for drug production are low, resulting in a low absorption rate in the human body.

As one solution to this problem, ZnPc derivatives such as tetrasulfonated ZnPc (ZnPcS$_4$), [1,2,3,4-tetrakis (α/β-D-galactopyranos-6-yl)-phthalocyaninato]zinc, and tetra- and octa-triethyleneoxysulfonyl substituted ZnPc have been designed to improve water solubility.

However, this approach requires a multi-step complex chemical functionalization process, which has risk of destroying the original, strongly bonded electronic system of the photosensitizer. Therefore, the approach has a problem in that the photoactivity of the photosensitizer is significantly reduced during the functionalization step. In addition, in the case where this complex chemical functionalization step is used, there is a problem that the efficacy decreases and the production cost increases.

Therefore, there is an urgent need for research on the development of new technologies to stably improve the absorption rate of photosensitizers in the human body by increasing the dispersibility of the photosensitizers that are intrinsically poorly dispersible.

DISCLOSURE

Technical Problem

The present disclosure has been made to solve the problems occurring in the related art, and the objective of the present disclosure is to propose highly dispersible zinc phthalocyanine-silica nanotubes capable of improving the dispersibility of zinc phthalocyanine to stably increase the absorption rate of zinc phthalocyanine in the human body and to propose a method of preparing highly dispersible zinc phthalocyanine-silica nanotubes.

Technical Solution

To achieve the objective, the present disclosure proposes a method of preparing highly dispersible zinc phthalocyanine-silica nanotubes, the method including: a first step of preparing a nanotube solution containing a nanotube template by mixing an alcohol solution with the nanotube template; a second step of preparing a zinc phthalocyanine (ZnPc) solution in which a zinc phthalocyanine complex compound is bound to the nanotube template by adding a zinc phthalocyanine (ZnPc) solution to the nanotube solution and by stirring the mixture; a third step of preparing a zinc phthalocyanine-silica nanotube solution by adding a silica precursor to the zinc phthalocyanine-nanotube solution, stirring the mixture, and silicifying the mixture; and a fourth step of filtering and drying the zinc phthalocyanine-silica nanotube solution to prepare zinc phthalocyanine-silica nanotube powder in which hydrophobic zinc phthalocyanine is adsorbed on and dispersed in silica nanotubes having pores having a size of 30 to 50 nm. The zinc phthalocyanine is dispersed by the silica nanotubes and exhibits dispersion stability in an aqueous solution.

Preferably, a template agent used in the first step is a peptide containing a glycylalkyl amide having an alkyl group having 8 to 18 carbon atoms.

Preferably, the silica precursor used in the third step is one or more selected among tetraethyl orthosilicate (TEOS), tetramethyl orthosilicate (TMOS), tetrapropyl orthosilicate (TPOS), tetrabutyl orthosilicate (TBOS), tetra pentyl orthosilicate (TPEOS), tetra(methylethylketoxime)silane, vinyl oximino silane (VOS), phenyl tris(butan-2-one oxime)silane (POS), and methyl oximino silane (MOS).

To achieve the objective described above, the present disclosure proposes highly dispersible zinc phthalocyanine-silica nanotubes prepared by the method described above.

Advantageous Effects

The highly dispersible zinc phthalocyanine-silica nanotubes and the preparation method thereof according to the present disclosure have the effects described below.

First, zinc phthalocyanine-silica nanotubes have the effect of being able to mass-produce zinc phthalocyanine at a low cost compared to the existing pure zinc phthalocyanine alone because zinc phthalocyanine is highly dispersed and adsorbed on silica nanotubes.

Second, zinc phthalocyanine-silica nanotubes have good stability because silica nanotubes are used as a medium. Therefore, the zinc phthalocyanine-silica nanotubes have the effect of high dispersibility that is maintained under any conditions such as any kind of solvent conditions.

Third, zinc phthalocyanine-silica nanotubes are in a form in which zinc phthalocyanine is adsorbed onto silica nanotubes having pores having a size of 30 to 50 nm. Since the length of each of the nanotubes is only several tens of micrometers, the nanotubes solve the problem of low adsorption on skin tissue, thereby improving the absorption rate of zinc phthalocyanine in the human body.

DESCRIPTION OF DRAWINGS

FIG. 3 illustrates a Raman analysis result of silica nanotubes according to the preferred embodiment of the present disclosure.

BEST MODE

Figure 1:
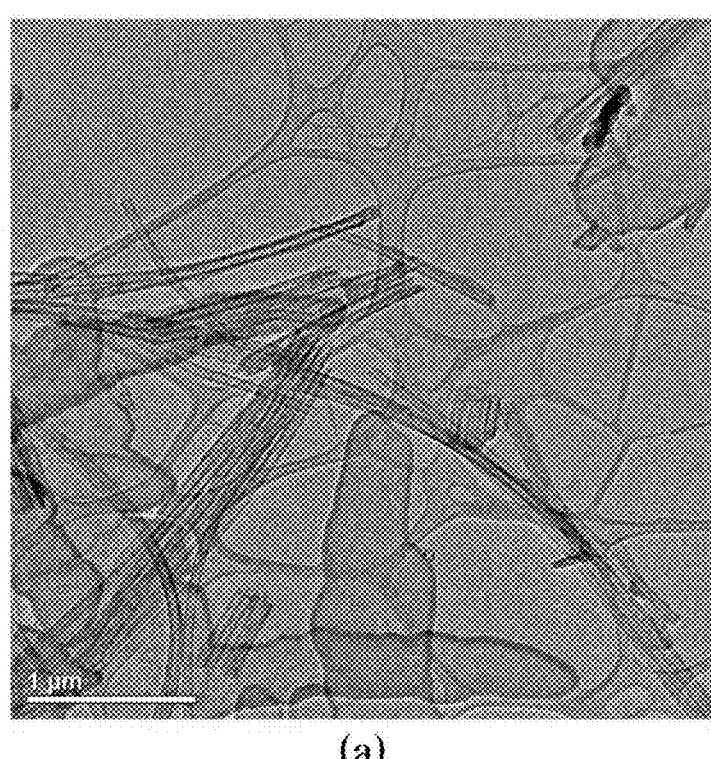
FIG. 1 is a TEM image of zinc phthalocyanine-silica nanotubes according to a preferred embodiment of the present disclosure.
Figure 1:
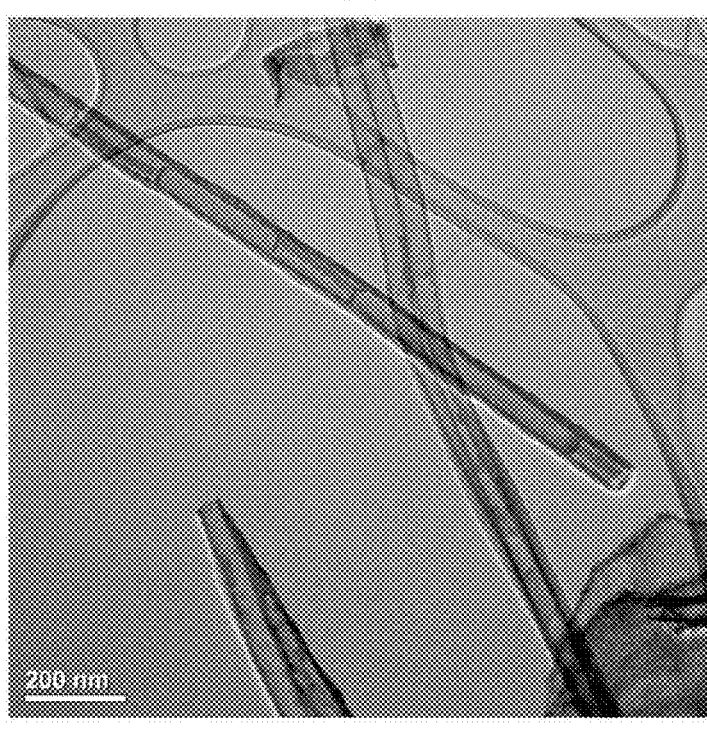

Hereinafter, the best mode of the present disclosure will be described with reference to preferred examples.

That is, highly dispersible zinc phthalocyanine-silica nanotubes according to the present disclosure can be prepared through a first step S10, a second step S20, a third step S30, and a fourth step S40. Each step has characteristics described below.

The first step S10 is a step of preparing a nanotube solution containing nanotube templates by mixing an alcohol solution with nanotube templates.

The first step is a step of preparing nanotube templates. In this step, a template agent is added to an alcohol solution, and the resulting mixture is heated and stirred at 55° C. to 65° C. until the alcohol solution becomes transparent. Next, the transparent solution is cooled to room temperature, then stirred at 1° C. to 5° C. for 30 to 90 minutes to obtain nanotube templates.

The template agent serves to form a backbone structure to obtain a nanotube shape, and a peptide template may be used as the template agent. Examples of the peptide may be glycylalkyl amides having an alkyl group having 8 to 18 carbon atoms. Among them, one or more compounds selected among glycyldodecylamide (GDA), 2-amino-N-dodecylacetamide, 2-amino-N-decylacetamide, and 2-amino-N-tetradecylacetamide may be used as the template agent.

The alcohol solution is prepared by mixing 90 to 95 wt % of purified water and 5 to 10 wt % of alcohol to completely dissolve the template agent. When the content of alcohol is less than 5 wt %, the template agent cannot completely dissolve. On the other hand, when the content of alcohol exceeds 10 wt %, since the concentration of the template agent is excessively thin, the overall reaction is slow, resulting in a long time to obtain the nanotube templates. Therefore, it is preferable that 90 to 95 wt % of purified water and 5 to 10 wt % of alcohol are mixed. As the alcohol, at least one selected among methanol ($CH_3OH$), ethanol ($C_2H_5OH$), propanol ($C_3H_7OH$), butanol ($C_4H_9OH$), and pentanol ($C_5H_{11}OH$) may be used.

For example, 15 to 25 mL of purified water and 1 to 5 mL of alcohol may be mixed for 1 mmol of the template agent. When the amount of the alcohol used is below the range, the template agent does not dissolve well and the reaction does not occur easily. On the other hand, when the amount of the alcohol used exceeds the range, the yield of production of nanotube templates is low due to difficulty in self-assembling. Therefore, it is preferable to appropriately control the amount of the alcohol used to fall within the range.

Stirring is carried out under a temperature condition of 55° C. to 65° C. so that the template agent can easily dissolve in the alcohol solution. When the temperature is below the range, it takes a long time for the template agent to dissolve in the alcohol solution whereas when the temperature is above the range, the alcohol solution boils and overflows, resulting in loss of alcohol and adverse effects on the properties of templates to be obtained. Therefore, the stirring may be carried out at 55° C. to 65° C. and preferably at 60° C.

When the alcohol solution to which the template agent is added becomes completely transparent, the mixture is cooled to room temperature, and then stirred for 30 to 90 minutes at 1° C. to 5° C. When the stirring time is shorter than 30 minutes or the temperature is below 1° C., it is difficult to control the size of nanotube templates to fall within the desired size range. In addition, when the stirring time is longer than 90 minutes or the temperature exceeds 5° C., it is also difficult to control the size of nanotube templates to fall within the desired range. Therefore, it is preferable that the stirring be performed at 1° C. to 5° C. for 30 to 90 minutes and more preferably at 2° C. for 30 minutes. When the stirring is performed under the conditions, it is possible to obtain nanotube templates having the desired size.

Next, the second step S20 is a step of preparing a zinc phthalocyanine-nanotube solution. A zinc phthalocyanine (ZnPc) solution is added to the nanotube solution prepared through the first step and the resulting mixture is stirred, so that the zinc phthalocyanine can be well dispersed. Through this step, the zinc phthalocyanine-nanotube solution in which a zinc phthalocyanine complex compound is bound to the nanotube templates is obtained.

In this case, the zinc phthalocyanine complex compound refers to a complex compound containing zinc phthalocyanine whose central metal ions are Zn(II) ions among metal salt-based phthalocyanines. In the present disclosure, ZnPc is an abbreviation for zinc phthalocyanine. That is, ZnPc and zinc phthalocyanine should interpreted as the same term in the present disclosure.

To form the zinc phthalocyanine complex compound in nanotubes, 1 to 10 mL of the zinc phthalocyanine solution having a concentration of 0.01 mmol may be added per 1 mmol of the template agent. When the amount of the zinc phthalocyanine solution added to the nanotube solution is smaller than 1 mL, it is difficult to form the zinc phthalocyanine complex compound in the nanotubes. On the other hand, when the amount of the zinc phthalocyanine solution added to the nanotube solution is 10 mL, the entire amount of the zinc phthalocyanine complex compound cannot bind to the nanotubes so that a portion of the zinc phthalocyanine complex compound may be present in the solution. Therefore, the amount of the added zinc phthalocyanine solution per 1 mmol of the template agent is in a range of 1 to 10 mL and more preferably is 5 mL.

Next, the third step S30 is a step of preparing a zinc phthalocyanine-silica nanotube solution by adding a silica precursor to the zinc phthalocyanine-nanotube solution and stirring the resulting mixture for silication. In this step, the silica precursor is added to the zinc phthalocyanine-nanotube solution, and the mixture is vigorously stirred for 30 to 90 minutes. Then, the resulting solution is stored in a static condition at room temperature for 1 to 5 days so that the silica precursor is gelated to produce a phthalocyanine-silica nanotube solution.

In this regard, after the addition of the silica precursor to the zinc phthalocyanine-nanotube solution, when the stirring time is shorter than 30 minutes, it takes a long time to obtain silica nanotubes. On the other hand, when the stirring time is longer than 90 minutes, the zinc phthalocyanine-silica nanotube solution may undergo change in the properties thereof. Therefore, the vigorous stirring is preferably performed for 30 to 90 minutes after the addition of the silica precursor to the zinc phthalocyanine-nanotube solution.

After the stirring, when the storage time is shorter than 1 day, stabilization of the zinc phthalocyanine-silica nanotube solution is insufficient. When the storage time is longer than 5 days, the improvement in the effect of the static condition storage is insignificant. Therefore, after the stirring of the zinc phthalocyanine-nanotube solution in which the silica precursor is contained, the zinc phthalocyanine-nanotube solution needs to be stored in a static condition preferably for 1 to 5 days and more preferably for 3 days. In this case, the silica precursor can be stably gelated and the silication can be stably performed so that the stabilization of physical properties can be obtained.

Here, examples of the silica precursor include tetraethyl orthosilicate (TEOS), tetramethyl orthosilicate (TMOS), tetra(methylethylketoxime)silane, vinyl oximino silane (VOS), phenyl tris(butan-2-one oxime)silane (POS), and methyl oximino silane (MOS). One or more compounds selected among them may be used. However, the silica precursor that can be used in the present disclosure is not limited thereto, and various silica precursors can be used as long as they can form silica nanotubes.

Here, the silica precursor may be added in an amount of 1 to 10 mmol per 1 mmol of the template agent. When the silica precursor that is added is less than 1 mmol, the thickness of a silica film is insufficient, resulting in silica nanotubes being in insufficient in structural stability thereof. When it exceeds 10 mmol, silica nanotubes with a multiwall structure may be formed, thereby impairing the function of zinc phthalocyanine. Therefore, the silica precursor may be used preferably in an amount of 1 to 10 mmol and more preferably in an amount of 4 mmol.

Finally, the fourth step S40 is a step of preparing zinc phthalocyanine-silica nanotube powder by filtering and drying the zinc phthalocyanine-silica nanotube solution. Specifically, the zinc phthalocyanine-silica nanotube solution in which the zinc phthalocyanine is highly dispersed is filtered to remove a liquid phase, and the remaining sold particles are washed with distilled water to remove impurities. The washed solid particles are dried at room temperature for 1 to 3 days through a vacuum drying process, to produce silicon nanotubes in a powder form.

In the zinc phthalocyanine-silica nanotube powder produced through these processes, zinc phthalocyanine is absorbed on silica nanotubes in a highly dispersed state.

Therefore, with the use of the preparation method described above, zinc phthalocyanine can be mass-produced at relatively low cost compared to conventional pure zinc phthalocyanine.

In addition, the zinc phthalocyanine-silica nanotubes prepared by the above preparation method are easy to functionalize on the surface, have high dispersibility in various solvents, are eco-friendly, are produced at competitive cost due to the reusability of templates, and are diversely usable.

The zinc phthalocyanine-silica nanotube powder has high dispersibility so that the dispersing power thereof in any kind of solvent or under any conditions can be maintained.

In addition, the zinc phthalocyanine-silica nanotube powder is powder in which zinc phthalocyanine is adsorbed to silica nanotubes with pores of having a size of 30 50 nm. In addition, since the full length of each of the nanotubes is only about several tens of micrometers, the nanotubes are free of problems such as adsorption to the skin tissue.

Another specific embodiment to achieve the objective of the present disclosure proposes highly dispersible zinc phthalocyanine-silica nanotubes containing zinc phthalocyanine, a template agent, and silica, in which the silica-nanotube has a structure in which the silica is bound to the template agent, and the zinc phthalocyanine is adsorbed to silica nanotubes.

The definitions of the zinc phthalocyanine, the template agent, and the silica are the same as defined above.

The template agent is preferably a peptide formed of a glycylalkyl amide having an alkyl group having 8 to 18 carbon atoms.

The silica is derived from one or more silica precursors such as tetraethyl orthosilicate (TEOS), tetramethyl orthosilicate (TMOS), tetrapropyl orthosilicate (TPOS), tetrabutyl orthosilicate (TBOS), tetrapropyl orthosilicate (TPEOS), tetra(methylethylketoxime)silane, vinyl oximino silane (VOS), phenyl tris(butan-2-one oxime)silane (POS), and methyl oximino silane (MOS), but is not necessarily limited thereto.

The definition of the silica precursor is the same as defined above.

The silica nanotube is provided with pores having a size of 30 to 50 nm. The pores of the silica nanotube are defined in the same way as previously defined.

The zinc phthalocyanine-silica nanotube preferably has a BET surface area of 250 to 400 m$^2$/g.

The volume of the pores is preferably 0.9 to 1.1 cm$^3$/g.

When the BET surface area and the pore volume are below the above ranges, respectively, since the formation of the pores is not sufficient, it is difficult for zinc phthalocyanine difficult to enter into the silica nanotubes. That is, the adsorption of zinc phthalocyanine to the silica nanotubes is poor. When the BET surface area and the pore volume exceed the above ranges, respectively, since the pores of the silica nanotubes have an excessively large size, the obtained zinc phthalocyanine silica-nanotubes are unstable in structure.

Hereinafter, examples of the highly dispersible zinc phthalocyanine-silica nanotubes and the preparation method thereof according to the present disclosure will be described. The examples below are provided only to aid understanding of the present disclosure and thus should not be construed as limiting to the scope of the present invention.

Example 1

1 mmol of glycyldodecylamide (GDA) was used as a gel-generator, and 20 mL of water and 2 mL of ethanol were added to the GDA and heated until the resulting solution became transparent, followed by stirring at 2° C. for about 1 hour. Next, 5 mL of an aqueous solution containing about 0.01 mmol of zinc phthalocyanine (ZnPc) (in the form of nanostructures or general reagents provided by Postech) was added to the solution, followed by stirring with a magnetic bar for an additional 10 minutes to form a complex compound. Then, 4 mmol of TEOS was further added thereto, stirred vigorously for about 1 hour, and stored at room temperature in a static condition for 3 days. The finished sample was filtered to remove a liquid phase, and impurities were washed off using distilled water, followed by vacuum drying at room temperature for 2 days. Thus, zinc phthalocyanine-silica nanotubes were obtained.

FIGS. 1-(a) and 1-(b) are TEM images of the zinc phthalocyanine-silica nanotubes prepared in Example 1. Specifically, FIG. 1-(a) is an image with a magnification showing the size of micrometers, and FIG. 10-(b) is an image with a magnification showing the size of nanometers. From the images, it was confirmed that the zinc phthalocyanine-silica nanotubes prepared according to Example 1 had a long channel shape with an inner diameter of about 40 nm.

In addition, a nitrogen adsorption analysis of the zinc phthalocyanine-silica nanotubes prepared in Example 1 was performed using the Barrett, Joyner and Halenda method. The result showed that the BET surface area was 325 m²/g, the pore volume was 1.03 cm³/g, and the average pore size was 38 nm.

Figure 2:
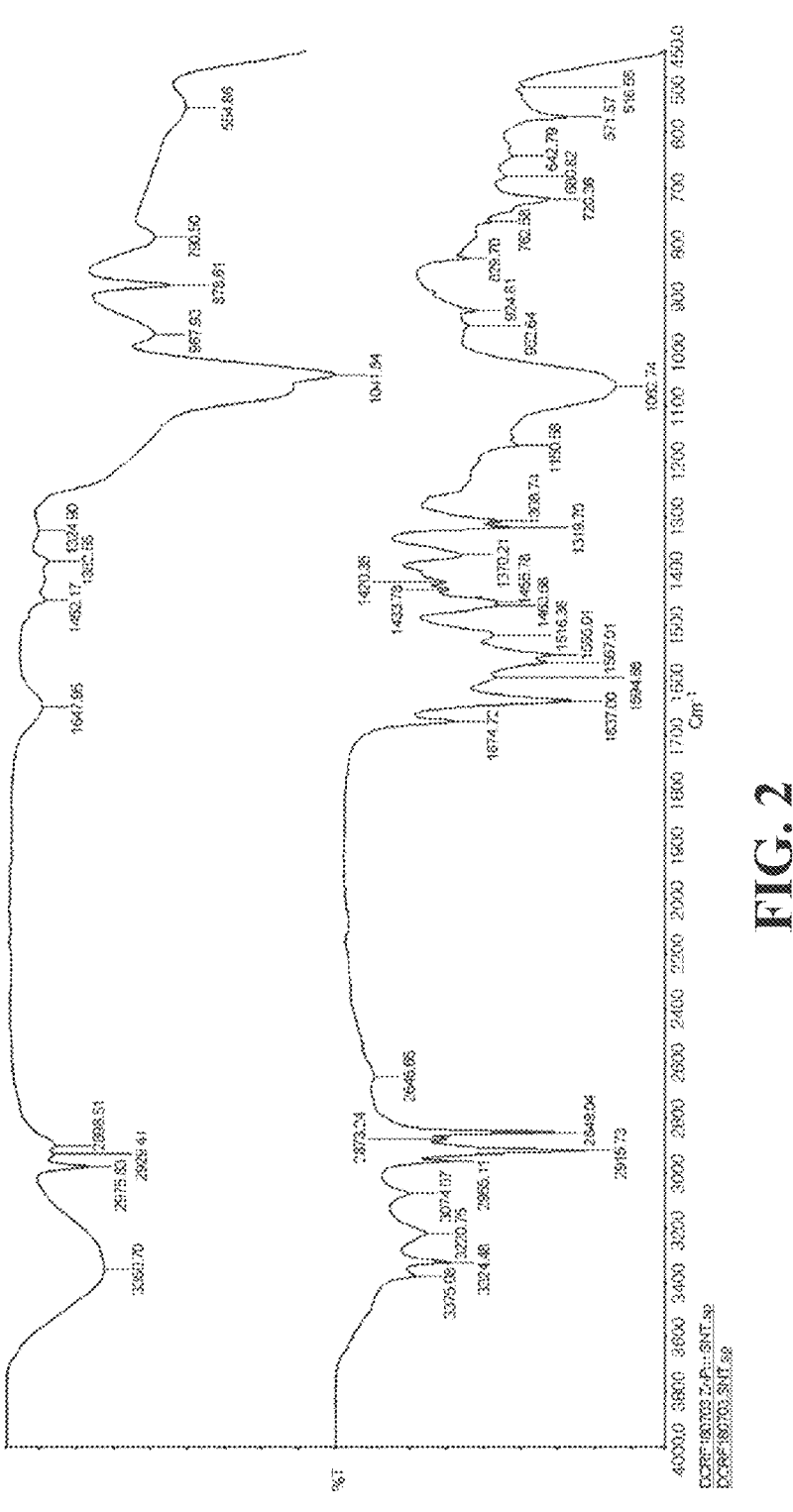
FIG. 2 illustrates a FT-IR result of the zinc phthalocyanine-silica nanotubes according to the preferred embodiment of the present disclosure.

To check whether the zinc phthalocyanine particles are adsorbed and reacted to the silica nanotubes prepared according to Example 1, Fourier-transform infrared spectroscopy (FTIR) was performed. The results are shown in FIGS. 2-(a) and 2-(b). FIG. 2-(a) is the FT-IR result of silica nanotubes, and FIG. 2-(b) the FT-IR result of zinc phthalocyanine-silica nanotubes in the form in which zinc phthalocyanine is dispersed in silica nanotubes.

Referring to FIGS. 2-(a) and 2-(b), as shown in FIG. 2-(b), the peak at around 3,074 cm⁻¹ is attributable to the stretching vibration of C—H of an aromatic ring, and the peak at around 1,637 cm⁻¹ is attributable to the stretching vibration of CN. The presence of such a series of peaks indicates the existence of phthalocyanine rings, which clearly shows the typical characteristics of ZnPc. The FT-IR results of the zinc phthalocyanine-silica nanotubes show that ZnPc nanoparticles and silicon nanoparticles both are present.

Figure 3:
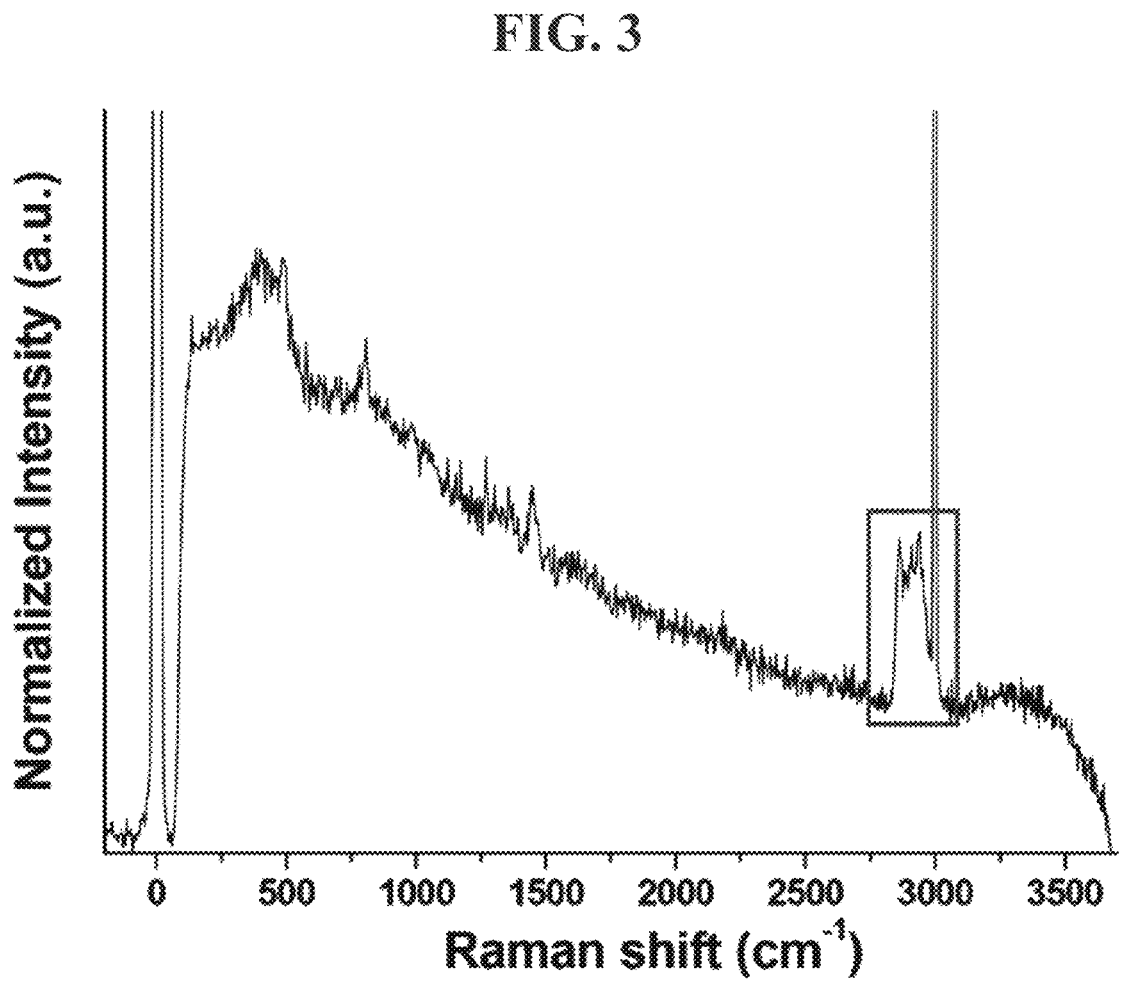
Figure 4:
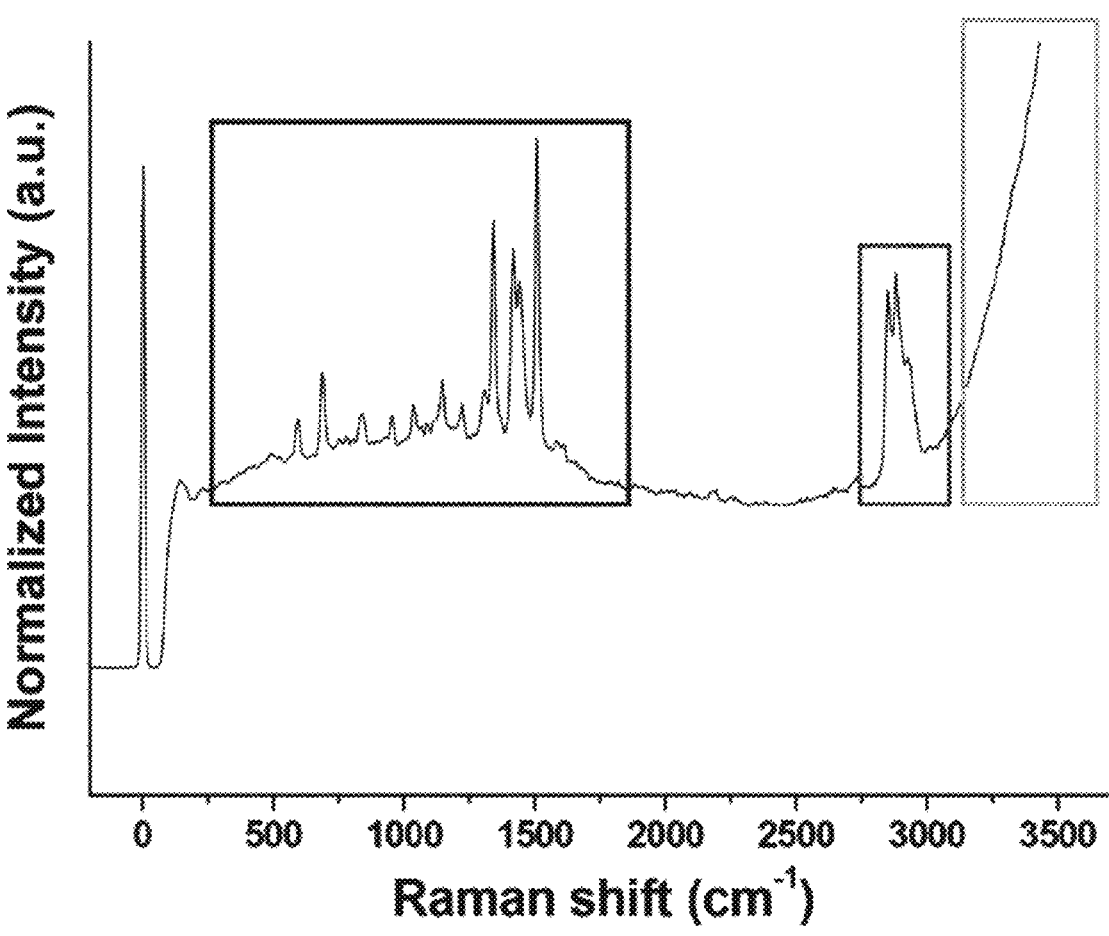
FIG. 4 is a diagram illustrating a Raman analysis result of the zinc phthalocyanine-silica nanotubes according to the preferred embodiment of the present disclosure.

FIG. 3 is a Raman analysis result of silica nanotubes, and FIG. 4 is a Raman analysis result of the zinc phthalocyanine-silica nanotubes prepared in Example 1. By comparing the simulation result and the test result and checking whether the Raman shifts thereof are identical, it is possible to find whether the detected materials are the same or not.

Specifically, referring to FIG. 3, a green part is the characteristic Raman peak of the silica nanotube. Referring to FIG. 4, a peak on a green part of FIG. 4 shows a Raman shift similar to that of the green part of FIG. 3. On the basis of the results of FIGS. 3 and 4, it can be confirmed that silica nanotubes are present. However, a high peak appearing in the vicinity of 3,000 cm⁻¹ is observed only in FIG. 3, indicating that zinc phthalocyanine affected the structure or vibration mode of the silica nanotube when the zinc phthalocyanine was added.

Figure 5:
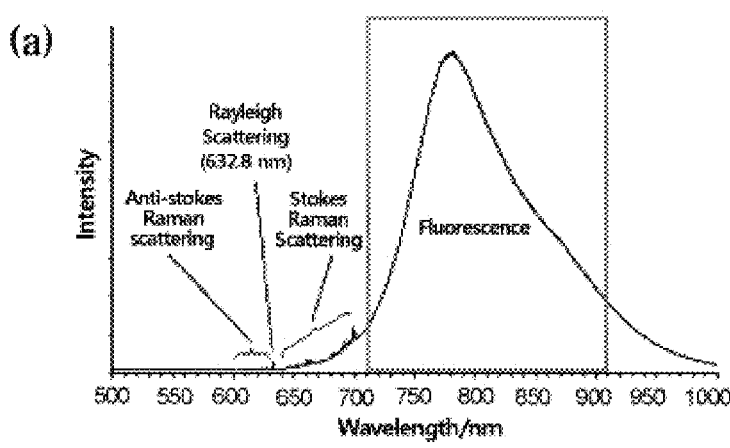
FIG. 5 is a diagram illustrating a Raman spectra reference for ZnPc.
Figure 5:
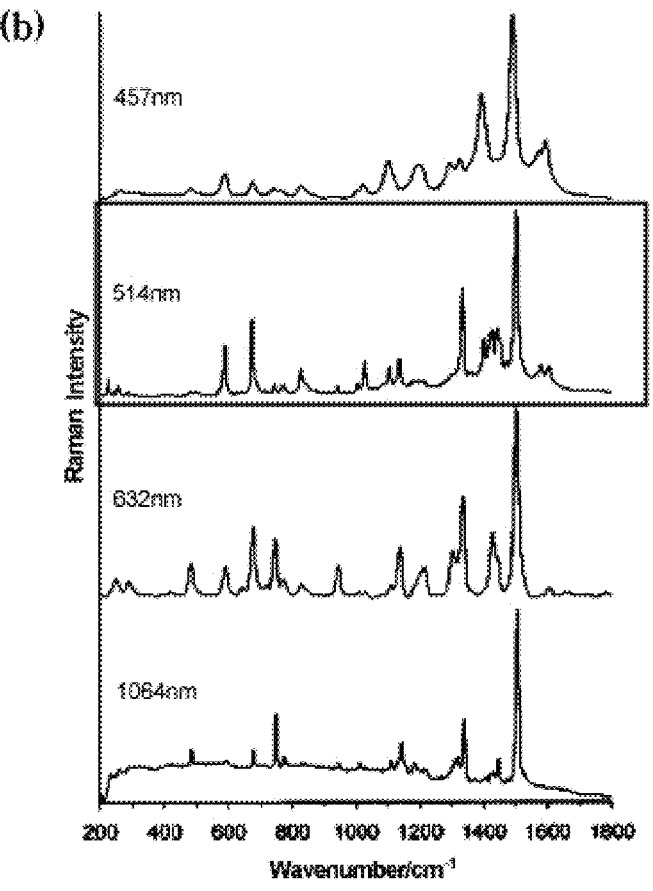

FIGS. 5A and 5B are Raman spectra references for ZnPc. FIG. 5A shows Raman data of ZnPc at 632.8 nm, and FIG. 5B shows Raman data of ZnPc at various wavelengths.

Referring to FIGS. 4, 5A, and 5B, a blue part of FIG. 4 is the same as the Raman peak of ZnPc shown on a blue part in FIG. 5B, and a yellow part of FIG. 4 represents fluorescence. These results show that ZnPc exhibiting fluorescence is present.

In summary, the presence of silica nanotubes was confirmed on the basis of the analysis results of FIGS. 3 and 4, and the presence of ZnPc was confirmed on the basis of the analysis results of FIGS. 4, 5A, and 5B. That is, it was confirmed that zinc phthalocyanine was dispersed in silica nanotubes.

Experimental Example 1

In this experimental example, the dispersion stability of highly dispersible zinc phthalocyanine-silica nanotubes was tested. The dispersion stability analysis was performed with the use of LUMiSizer™. Using this, the average value of all the transmittance profiles generated during the measurement period was displayed over time to analyze the dispersion stability.

In this regard, the dispersion stability refers to the stability of a dispersed material, and the longer the dispersion state is maintained after being dispersed, the higher the dispersion stability. As a measurement method, there is a method of directly observing the change in dispersion stability of the sample. In this regard, to shorten the observation time, there is a method of letting the sample to experience harsh conditions such as centrifugal force or heating so that the change in dispersion stability of the sample can be checked in a quick time (refer to "Procedures to accelerate the evaluation of long-term stability", ISO/TR 13097). For example, the sample may undergo centrifugation so that relatively quick sedimentation of particles can occur compared to gravity sedimentation. In this case, layer separation occurs. Next, the sample is irradiated with near infrared (IR) rays having a wavelength of 865. At this time, a portion of the IR rays may be absorbed by the sample, and the remaining portion of the IR rays can transmit through the sample. A detector detects the IR rays having transmitted through the sample, and the detected rays are represented in real time as a transmittance profile. It is a method of performing comparative analysis of dispersion stability between samples by quantifying the generation rate, pattern, etc. of such a profile.

The dispersion conditions and analysis conditions are described below.

Dispersion Conditions

Dispersion device: VCX-750 Ultrasonicator Processor (Manufacturer: Sonics & Materials, Inc., USA)

Probe: 13-mm probe

Amplitude: 80%

Total dispersing time: 10 minutes per sample

Analysis Conditions

Analysis instrument: LUMiSizer (Manufacturer: LUM GmbH, Germany)

Intervals: 5 seconds

PA 2-mm cell

Total test time: 55 seconds

Sample

Figure 6:
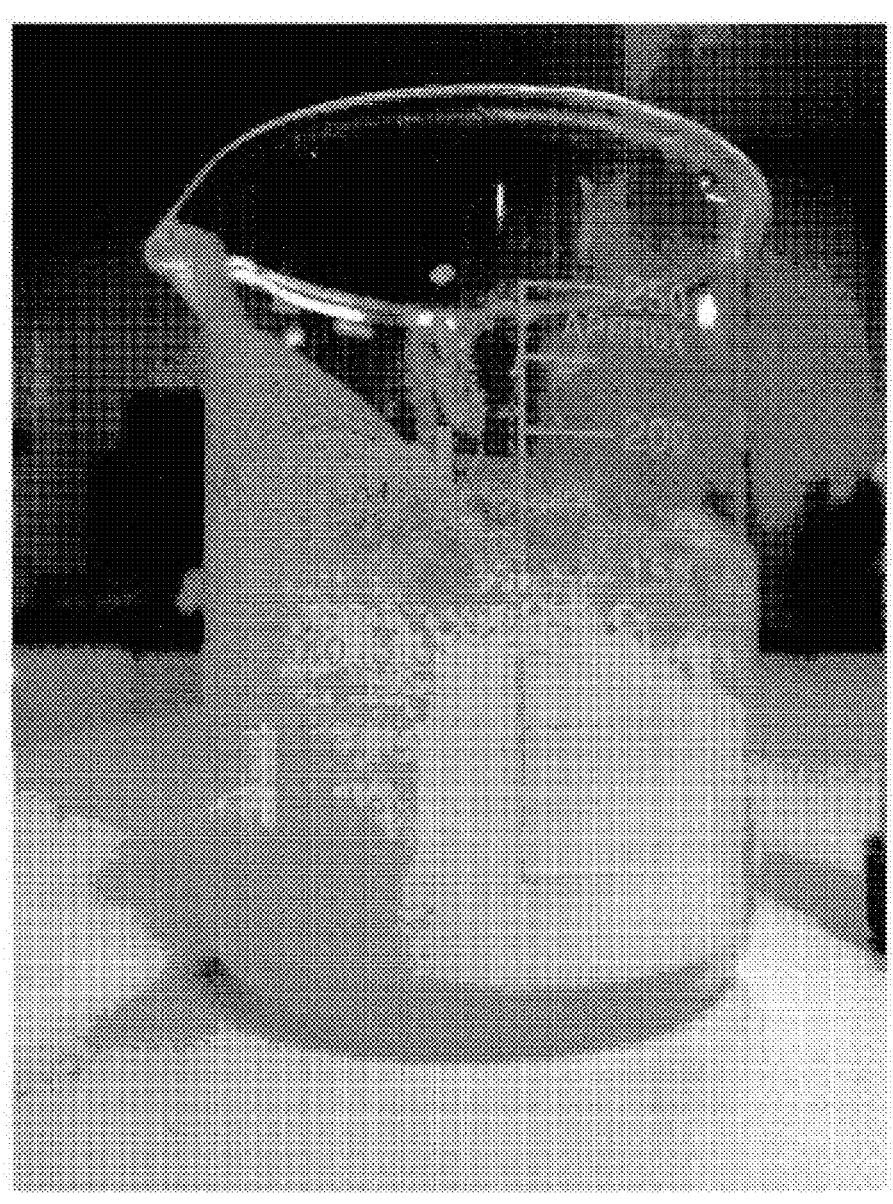
FIG. 6 illustrates Test Group I of the present disclosure.

Test Group I is 50 ml of a silica nanotube dispersion solution obtained by dissolving 25 mg of silica nanotubes in 250 mL of water to obtain an intermediate solution and then by mixing 25 ml of the intermediate solution with 25 mL of water. FIG. 6 is a photograph illustrating Test Group I immediately after dispersion.

Figure 7:
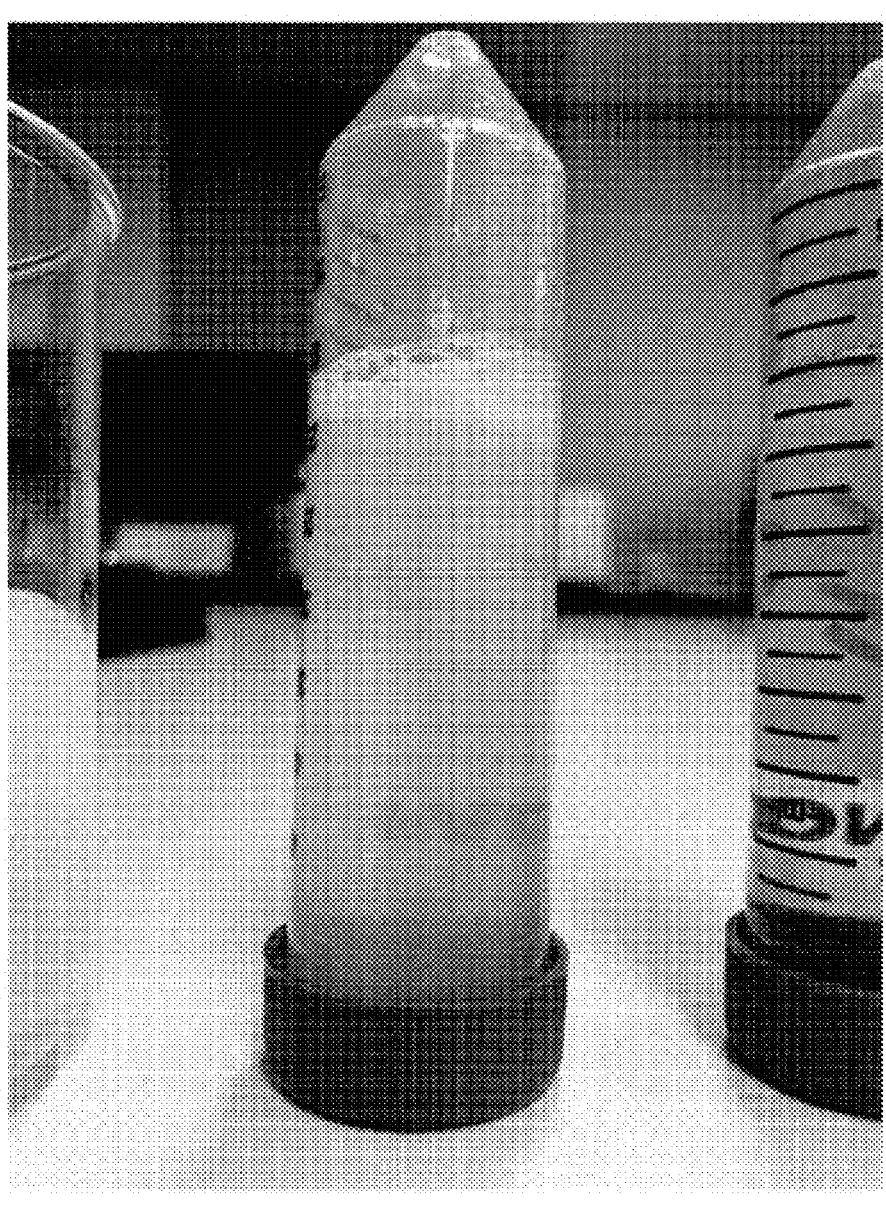
FIG. 7 illustrates Test Group II of the present disclosure.

Test Group II is a zinc phthalocyanine-silica nanotube dispersion solution in which 0.2 mg of zinc phthalocyanine is dispersed in 50 mL of the silica nanotube dispersion solution of Test Group I. FIG. 7 is a photograph illustrating Test Group II immediately after dispersion.

Figure 8:
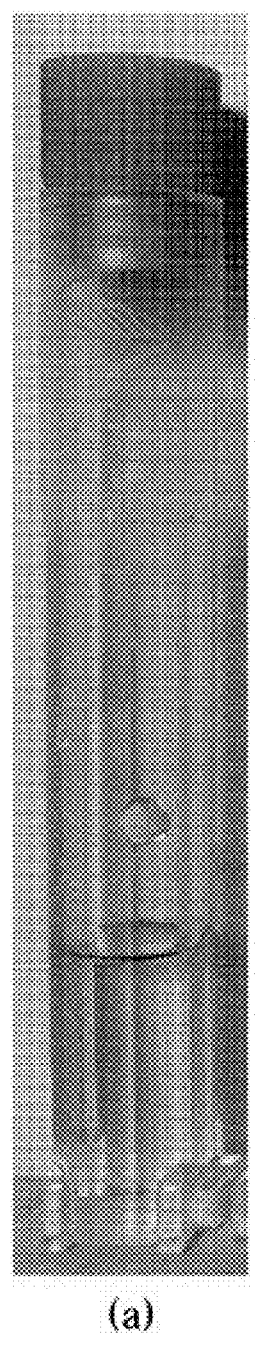
FIG. 8 illustrates a control group.
Figure 8:
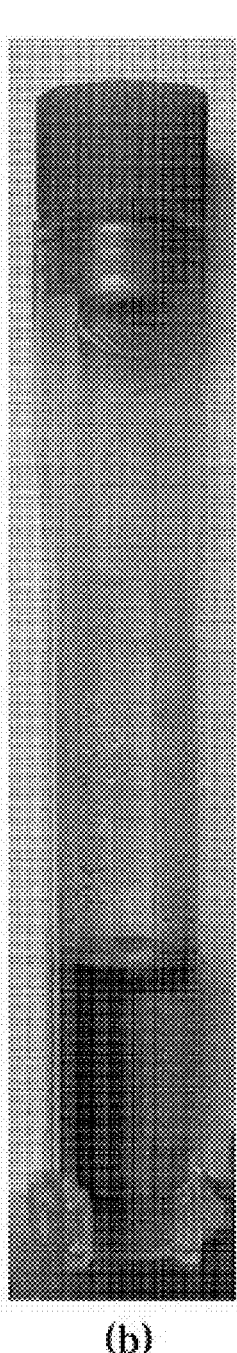

The control group is 50 mL of a zinc phthalocyanine dispersion solution in which 0.2 mg of zinc phthalocyanine is dispersed. In relation to this, FIGS. 8A and 8B are pictures illustrating a pre-dispersion state which is a state before dispersion of zinc phthalocyanine and a post-dispersion state which is a state after dispersion, respectively.

First, only Test Group I was measured for dispersion stability immediately after dispersing and after one day of storage from the dispersing. The results are shown in FIG. 9-(I).

Figure 9:
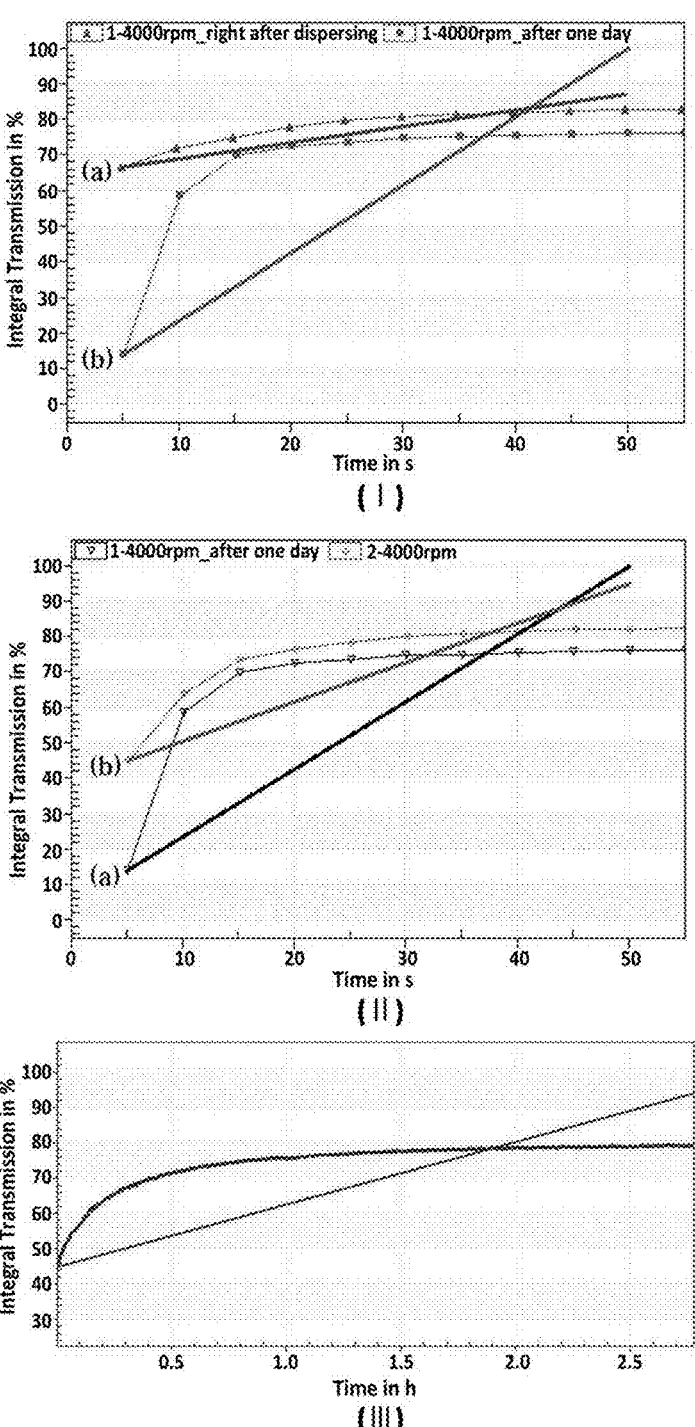
FIG. 9 is a graph showing the average value of the transmittance profile of Test group I, Test group II, and Control group of the present disclosure.

Referring to the drawings, FIG. 9-(I) is a graph showing the average value of the transmittance profile for Test Group I, and FIG. 9-(I)(a) shows that the average value (integral transmission in %) of the transmittance profile right after dispersing of Test Group I gradually increases with time, and FIG. 9-(I)(b) shows that the average value (integral transmission in %) of the transmittance profile for Test Group I gradually increases with time after one day of storage from the dispersing. Referring to FIG. 9-(I)(b), the average value (integral transmission in %) of the transmittance profile gradually increase after one day of storage from the dispersing. This is because particles in Test Group I are precipitated, separation of layers of Test Group progresses and a transparent layer gradually widens. As the transparent layer becomes wider, the value of the transmittance profile generated accordingly increases.

In addition, the steeper the increase slope (rate in %/s) of the average value of the transmittance profile, the faster the layer separation and the lower the dispersion stability. Conversely, the gentler the slope of the increase, the slower the layer separation, indicating that the dispersion stability is high.

Figure 10:
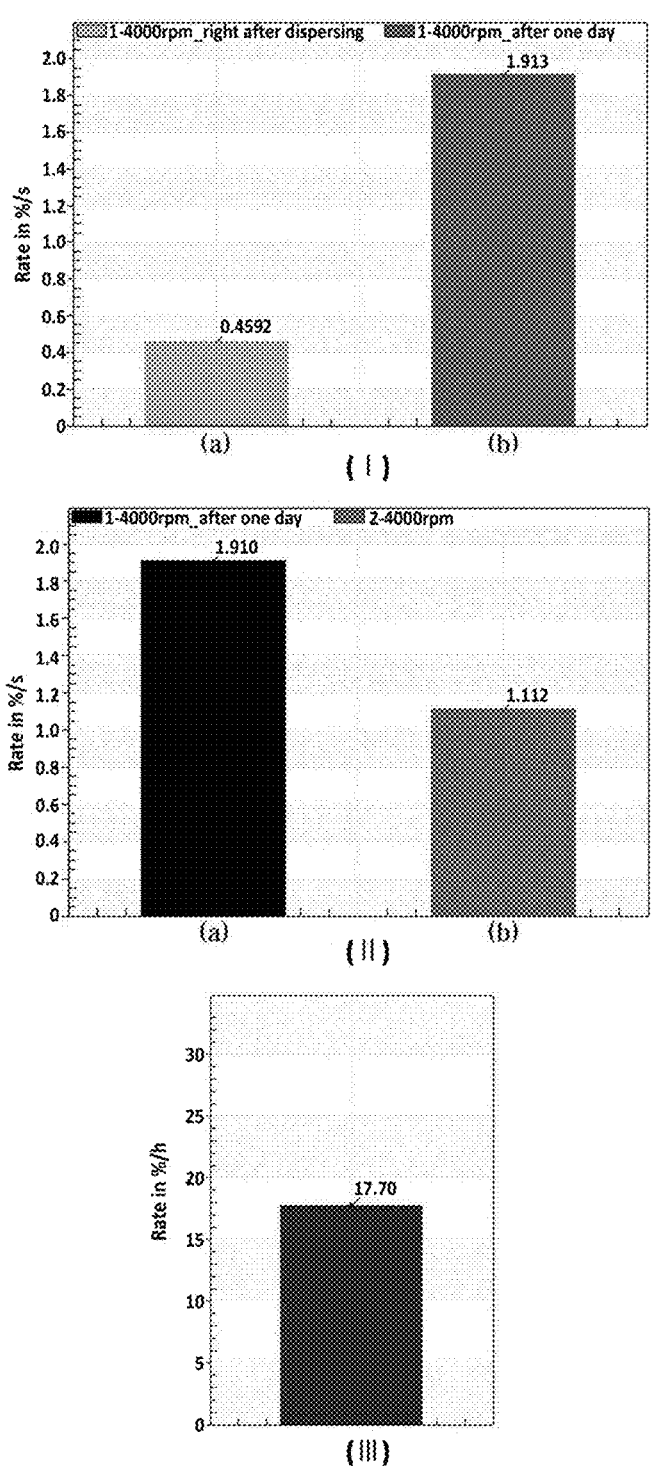
FIG. 10 is a graph illustrating an increase slope of data of FIG. 9.

The increase slope of FIG. 9-(I) was analyzed, and the result is shown in FIG. 10-(I). FIG. 10-(¬) is a graph showing the increase slope of FIG. 9-(¬). FIG. 10-(I)(a) illustrates an increase slope (rate in %/s) in the average value of the transmittance profile of Test Group I immediately after the dispersing, and FIG. 10-(I)(b) illustrates the increase slope (rate in %/s) in the average value of the transmittance profile of Test Group I after 1 day of storage after the dispersing.

Referring to FIG. 10(I), when the state of Test Group I immediately after the dispersing and the state of Test Group I after one day of storage from the dispersing are compared, since the increase slope (rate in %/s) of the average value of the transmittance profile after one day of storage is relatively steep, it is confirmed that the rate of formation of the transparent layer after one day of storage from the dispersing is 4.16 times higher than that of the sample immediately after the dispersing.

Next, the dispersion stability of Test Group II, in which zinc phthalocyanine was dispersed in silica nanotubes, was measured and compared with that of Test Group I in which only silica nanotubes were present and stored for one day after the dispersing. The results are shown in FIG. 9-(II).

Referring to the results, FIG. 9-(II) is a graph showing the average value of the transmittance profile of each of Test Group I and Test Group II. FIG. 9-(II)(a) shows that the average value (integral transmission in %) of the transmittance profile of Test Group I gradually changes after one day of storage from the dispersing, and FIG. 9-(II)(b) shows that the average value (integral transmission in %) of the transmittance profile of Test Group II gradually increases with time.

The increase slope of FIG. 9-(II) was analyzed, and the results are shown in FIG. 10-(II). FIG. 10-(II) is a graph showing the increase slope of FIG. 9-(II). FIG. 10-(II)(a) illustrates an increase slope (rate in %/s) of the average value of the transmittance profile of Test Group I after one day of storage from the dispersing, and FIG. 10-(II)(b) illustrates ab increase slope (rate in %/s) of the average value of the transmittance profile of Test Group II.

Referring to FIG. 10-(II), since the layer separation rate of Test Group I is about 1.72 times faster than that of Test Group II, the increase slope (rate in %/s) of the average value of the transmittance profile of Test Group II in which zinc phthalocyanine is dispersed in silica nanotubes was more gentle than that of Test Group I in which only silica nanotubes are present. Therefore, layer separation slowly occurs, indicating that the dispersion stability is high.

In addition, FIG. 9-(III) is a graph showing the average value of the transmittance profile of the control group, and FIG. 10-(III) illustrates the increase slope (rate in %/s) of the average value of the transmittance profile for the control group of FIG. 9-(III).

Table 1 below summarizes the increase slope (rate in %/s) of the average value of the transmittance profile of Test Group I and the increase slope (rate in %/s) of the average value of the transmittance profile of Test Group II.

TABLE 1

|  | Test Group I | Test Group II | Control Group |
|---|---|---|---|
| rate in %/s | 1.910 | 1.112 | 17.70 |

Referring to Table 1, since the increase slope of the average value of the transmittance profile of Test Group II is relatively gentler than that of the average value of the transmission profile of Test Group I compared to the control group in which only pure zinc phthalocyanine is present, the dispersion stability of Test Group II in which zinc phthalocyanine is dispersed in nanotubes is higher than that of Test Group I in which only silica nanotubes are present.

From the results of Examples and Experimental Examples, it can be confirmed that the hydrophobic zinc phthalocyanine is dispersed in and adsorbed to silica nanotubes, thereby high dispersibility and dispersion stability can be obtained. Therefore, the method of preparing a highly dispersible zinc phthalocyanine-silica nanotube according to the present disclosure invention improves the dispersibility of zinc phthalocyanine, thereby increasing the absorption rate of zinc phthalocyanine in the human body.

The embodiments that have been described herein above are merely illustrative of the technical idea of the present invention, and thus various modifications, changes, alterations, substitutions, subtractions, and additions may also be made by those skilled in the art without departing from the gist of the present disclosure.

The embodiments disclosed in the present disclosure are not intended to limit the scope of the present invention and the technical spirit of the present invention should not be construed as being limited to the embodiments.

The protection scope of the present disclosure should be construed as defined in the following claims, and it is apparent that all technical ideas equivalent thereto fall within the scope of the present invention.

11

The invention claimed is:

1. A method of preparing a highly dispersible zinc phthalocyanine-silica nanotube, the method comprising:

a first step of mixing a template agent and an alcohol solution to prepare a nanotube solution containing a nanotube template;

a second step of adding and dispersing a zinc phthalocyanine (ZnPc) solution to and in the nanotube solution by stirring, thereby preparing a zinc phthalocyanine-nanotube solution in which a zinc phthalocyanine complex compound is bound to the nanotube template;

a third step of adding a silica precursor to the zinc phthalocyanine-nanotube solution and stirring the resulting mixture for silication, thereby preparing a zinc phthalocyanine-silica nanotube solution; and a fourth step of filtering the zinc phthalocyanine-silica nanotube solution, followed by drying, to prepare zinc phthalocyanine-silica nanotube powder in which hydrophobic zinc phthalocyanine is adsorbed to and dispersed in silica nanotubes with pores having a size of 30 to 50 mm, wherein the zinc phthalocyanine is dispersed in an aqueous solution by silica nanotubes and has dispersion stability.

2. The method according to claim 1, wherein the template agent used in the first step is a peptide containing a glycylalkyl amide having an alkyl group having 8 to 18 carbon atoms.

3. The method according to claim 1, wherein the silica precursor used in the third step is one or more selected among tetraethyl orthosilicate (TEOS), tetramethoxyorthosilicate (TMOS), tetrapropyl orthosilicate (TPOS), tetrabutylortho silicates (TBOS), tetra pentylorthosilicate (TPEOS), tetra(methylethylketoxime)silane, vinyl oximino silane (VOS), phenyl tris (butan-2-one oxime) silane (POS), and methyl oximino silane (MOS).

4. A highly dispersible zinc phthalocyanine-silica nanotube prepared by the method according to claim 1.

5. A highly dispersible zinc phthalocyanine-silica nanotube containing a zinc phthalocyanine, a template agent, and silica, wherein a silica nanotube has a form in which silica is bound to a template agent, and the zinc phthalocyanine is adsorbed to the silica nanotube, wherein the highly dispersible zinc phthalocyanine-silica nanotube has a BET surface area of 250 to 400 $m^2/g$.

6. The highly dispersible zinc phthalocyanine-silica nanotube according to claim 5, wherein the template agent is a peptide containing a glycylalkyl amide having an alkyl group having 8 to 18 carbon atoms.

7. The highly dispersible zinc phthalocyanine-silica nanotube according to claim 5, wherein the silica is derived from one or more silica precursors selected among tetraethoxy orthosilicate (TEOS), tetra methoxyorthosilicate (TMOS), tetrapropyl orthosilicate (TPOS), tetrabutylortho silicates (TBOS), tetra pentylorthosilicate (TPEOS), tetra(methylethylketoxime) silane, vinyl oximino silane (VOS), phenyl tris(butan-2-one oxime) silane (POS), and methyl oximino silane (MOS).

8. The highly dispersible zinc phthalocyanine-silica nanotube according to claim 5, wherein the silica nanotube has a pore having a size of 30 to 50 nm.

9. The highly dispersible zinc phthalocyanine-silica nanotube according to claim 5, wherein the pore has a pore volume of 0.9 to 1.1 $cm^3/g$.

* * * * *